United States Patent [19]
Mitchell

[11] Patent Number: 6,039,629
[45] Date of Patent: Mar. 21, 2000

[54] NURSING PAD

[76] Inventor: Julia Mitchell, 16 Acorn Close, Bowerdean Road, High Wycombe Buckinghamshire HP13 6XE, United Kingdom

[21] Appl. No.: 09/307,347

[22] Filed: May 6, 1999

[51] Int. Cl.$^7$ .................................................... A41C 3/04
[52] U.S. Cl. .................................. 450/57; 450/37; 2/267
[58] Field of Search ........................ 450/37, 39, 30–32, 450/40, 57, 55, 56, 81; 2/267

[56] References Cited

U.S. PATENT DOCUMENTS

| 2,627,606 | 2/1953 | De Grandis | 450/37 |
|---|---|---|---|
| 2,891,544 | 6/1959 | London | 450/37 |
| 2,896,623 | 7/1959 | Fitzgerald | 450/37 |
| 3,301,254 | 1/1967 | Schickendanz | 450/37 |
| 3,356,090 | 12/1967 | Plantinga et al. | 450/37 |
| 4,047,534 | 9/1977 | Thomaschefsky et al. | 450/37 |
| 4,164,228 | 8/1979 | Weber-Unger | 450/37 |
| 5,017,174 | 5/1991 | Gowrylow | 450/37 |
| 5,690,536 | 11/1997 | Madden et al. | 450/37 |
| 5,782,672 | 7/1998 | Woodley | 450/37 |

*Primary Examiner*—Gloria Hale

[57] ABSTRACT

A nursing pad for absorbing milk leaking from a lactating user's nipple. The nursing pad includes a water impermeable exterior layer has a center region, an outer perimeter, a concave inner face, and a convex outer face. The inner face of the exterior layer defines an inner space in which a plurality of coextensive generally hemispherical inner layers are disposed. The plurality of inner layers comprises first, second, third and fourth inner layers: the first inner layer is positioned adjacent the inner face of the exterior layer; the second and third inner layers is interposed between the first and fourth inner layers; and the third inner layer is interposed between the second and fourth inner layers. The first and third inner layer each comprise a woven fabric material. The second inner layer comprises a water absorbing material. The fourth inner layer comprises a water permeable material.

8 Claims, 2 Drawing Sheets

NURSING PAD

BACKGROUND OF THE INVENTION

1. Field of the Invention

The present invention relates to nursing pads and more particularly pertains to a new nursing pad for absorbing milk leaking from a lactating user's nipple.

2. Description of the Prior Art

The use of nursing pads is known in the prior art. More specifically, nursing pads heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 4,700,699; U.S. Pat. No. 4,047,534; U.S. Pat. No. 4,875,492; U.S. Pat. No. 3,356,090; U.S. Pat. No. 5,017,174; and U.S. Pat. No. Des. 347,278.

While these devices fulfill their respective, particular objectives and requirements, the aforementioned patents do not disclose a new nursing pad. The inventive device includes a water impermeable exterior layer has a center region, an outer perimeter, a concave inner face, and a convex outer face. The inner face of the exterior layer defines an inner space in which a plurality of coextensive generally hemispherical inner layers are disposed. The plurality of inner layers comprises first, second, third and fourth inner layers: the first inner layer is positioned adjacent the inner face of the exterior layer; the second and third inner layers is interposed between the first and fourth inner layers; and the third inner layer is interposed between the second and fourth inner layers. The first and third inner layer each comprise a woven fabric material. The second inner layer comprises a water absorbing material. The fourth inner layer comprises a water permeable material.

In these respects, the nursing pad according to the present invention substantially departs from the conventional concepts and designs of the prior art, and in so doing provides an apparatus primarily developed for the purpose of absorbing milk leaking from a lactating user's nipple.

SUMMARY OF THE INVENTION

In view of the foregoing disadvantages inherent in the known types of nursing pads now present in the prior art, the present invention provides a new nursing pad construction wherein the same can be utilized for absorbing milk leaking from a lactating user's nipple.

The general purpose of the present invention, which will be described subsequently in greater detail, is to provide a new nursing pad apparatus and method which has many of the advantages of the nursing pads mentioned heretofore and many novel features that result in a new nursing pad which is not anticipated, rendered obvious, suggested, or even implied by any of the prior art nursing pads, either alone or in any combination thereof.

To attain this, the present invention generally comprises a water impermeable exterior layer has a center region, an outer perimeter, a concave inner face, and a convex outer face. The inner face of the exterior layer defines an inner space in which a plurality of coextensive generally hemispherical inner layers are disposed. The plurality of inner layers comprises first, second, third and fourth inner layers: the first inner layer is positioned adjacent the inner face of the exterior layer; the second and third inner layers is interposed between the first and fourth inner layers; and the third inner layer is interposed between the second and fourth inner layers. The first and third inner layer each comprise a woven fabric material. The second inner layer comprises a water absorbing material. The fourth inner layer comprises a water permeable material.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new nursing pad apparatus and method which has many of the advantages of the nursing pads mentioned heretofore and many novel features that result in a new nursing pad which is not anticipated, rendered obvious, suggested, or even implied by any of the prior art nursing pads, either alone or in any combination thereof.

It is another object of the present invention to provide a new nursing pad which may be easily and efficiently manufactured and marketed.

It is a further object of the present invention to provide a new nursing pad which is of a durable and reliable construction.

An even further object of the present invention is to provide a new nursing pad which is susceptible of a low cost of manufacture with regard to both materials and labor, and which accordingly is then susceptible of low prices of sale to the consuming public, thereby making such nursing pad economically available to the buying public.

Still yet another object of the present invention is to provide a new nursing pad which provides in the apparatuses and methods of the prior art some of the advantages thereof, while simultaneously overcoming some of the disadvantages normally associated therewith.

Still another object of the present invention is to provide a new nursing pad for absorbing milk leaking from a lactating user's nipple.

Yet another object of the present invention is to provide a new nursing pad which includes a water impermeable exterior layer has a center region, an outer perimeter, a concave inner face, and a convex outer face. The inner face of the exterior layer defines an inner space in which a plurality of coextensive generally hemispherical inner layers are disposed. The plurality of inner layers comprises first, second, third and fourth inner layers: the first inner layer is positioned adjacent the inner face of the exterior layer; the second and third inner layers is interposed between the first and fourth inner layers; and the third inner layer is interposed between the second and fourth inner layers. The first and third inner layer each comprise a woven fabric material. The second inner layer comprises a water absorbing material. The fourth inner layer comprises a water permeable material.

Still yet another object of the present invention is to provide a new nursing pad that prevents leaking milk for wetting the bra and garment of a user.

Even still another object of the present invention is to provide a new nursing pad that helps absorb leaking milk to keep the moisture away from the user's nipple to keep the delicate nipple region more comfortable and less irritated.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
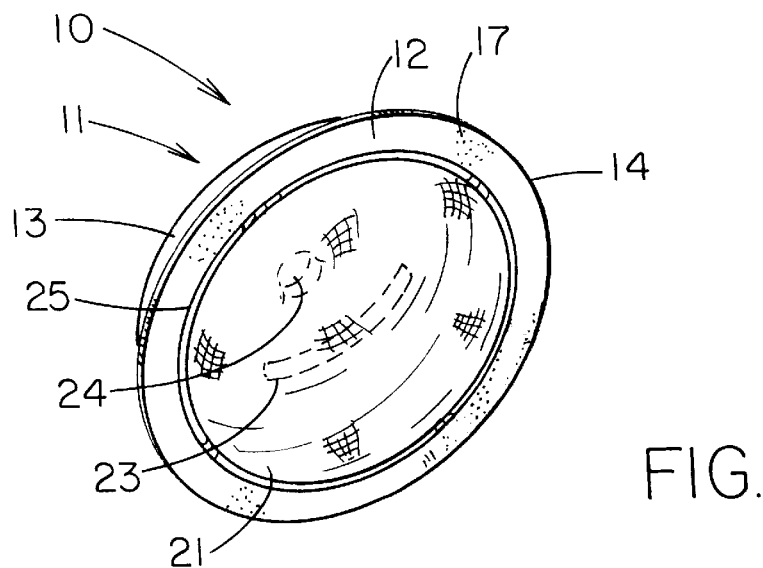
FIG. 1 is a schematic rear perspective view of a new nursing pad according to the present invention.

With reference now to the drawings, and in particular to FIGS. 1 through 4 thereof, a new nursing pad embodying the principles and concepts of the present invention and generally designated by the reference numeral 10 will be described.

As best illustrated in FIGS. 1 through 4, the nursing pad 10 generally comprises a water impermeable exterior layer has a center region, an outer perimeter, a concave inner face, and a convex outer face. The inner face of the exterior layer defines an inner space in which a plurality of coextensive generally hemispherical inner layers are disposed. The plurality of inner layers comprises first, second, third and fourth inner layers: the first inner layer is positioned adjacent the inner face of the exterior layer; the second and third inner layers is interposed between the first and fourth inner layers; and the third inner layer is interposed between the second and fourth inner layers. The first and third inner layer each comprise a woven fabric material. The second inner layer comprises a water absorbing material. The fourth inner layer comprises a water permeable material.

In use, the nursing pad 10 is designed for attachment to a cup of a user's bra so that it is interposed between the cup of the bra and the user's breast received in the cup of the bra. In closer detail, the nursing pad comprises a generally hemispherical cup shaped exterior layer 11 having a center region, a generally circular outer perimeter coaxial with the center region of the exterior layer, a concave inner face 12, and a convex outer face 13. The cup shape of the exterior layer is shaped to conform to the breast of the user and cup of a bra of the user.

The exterior layer has an outwardly radiating annular outer flange 14 around the outer perimeter of the exterior layer. The outer face of the exterior layer has an adhesive 15 provided thereon along the outer flange of the exterior layer. In use, the adhesive of the exterior layer is designed for adhesively coupling the outer flange to a cup of a bra of a user such that the exterior layer is received in the cup of the bra and the outer face of the exterior layer abuts an inner surface of the cup of the bra. Preferably, an annular protective strip 16 covering the adhesive. The protective strip is removably peelable from the adhesive such that a minimal amount of adhesive is retained on the protective strip.

The exterior layer comprises a flexible water impermeable material to prevent passage of water-based fluids such as milk therethrough. Ideally, the exterior layer comprises a flexible water impermeable plastic material. In such an ideal embodiment, the outer flange of the exterior layer has a plurality of apertures 17 (or pores) therethrough extending between the inner and outer faces of the exterior layer. In use, the apertures are designed enhancing the breathability through the exterior layer along the outer flange for additional user comfort.

The concave inner face of the exterior layer defining a generally hemispherical inner space. A plurality of coextensive generally hemispherical inner layers 18,19,20,21 are disposed in the inner space of the exterior layer. The plurality of inner layers comprises first, second, third and fourth inner layers each having centers coaxial with the center of the center of the exterior layer and each having a generally outer perimeter located inside and concentric with the outer perimeter of the exterior layer.

The first inner layer 18 is positioned adjacent the inner face of the exterior layer. The fourth inner layer 21 is exposed and facing outwards from the inner face of the exterior layer. The second and third inner layers 19,20 are interposed between the first and fourth inner layers with the third inner layer 20 interposed between the second and fourth inner layers 19,21.

Figure 2:
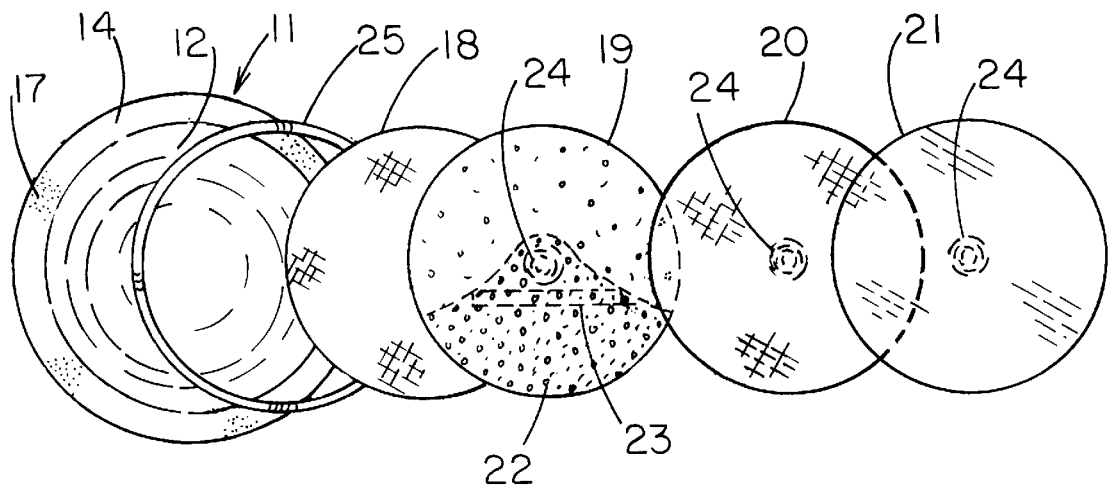
FIG. 2 is a schematic exploded rear view of the layers of the present invention.
Figure 3:
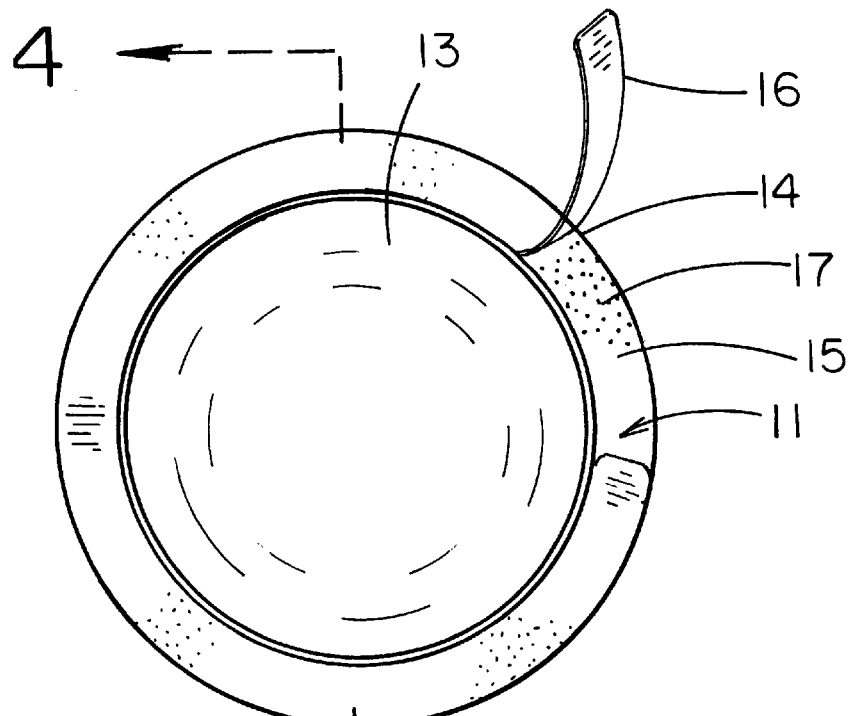
FIG. 3 is a schematic front view of the present invention.

The first and third inner layer each comprise a dry weave woven fabric material. The second inner layer comprises a water absorbing material. As best illustrated in FIG. 2, the second inner layer preferably has a generally triangular wedge shaped super absorbent lower region 22 comprising a water absorbent material having a greater absorption capacity than the remainder of the second inner layer. The lower region is extended around the center of the second inner layer to help absorb fluid in the regions most likely to receive leaking milk from the user's breast (i.e., the area of the second inner layer around and below the user's nipple). Ideally, the second inner layer has a guide line 23 displayed on a face of the second inner layer facing outwards away from the inner face of the exterior layer, the guide line is positioned between the lower region of the second inner layer and the center of the second inner layer, the guide line is designed for indicating to a user where the lower region of the second inner layer is so that the user can position the nursing pad in the cup of the bra of the user with the lower region of the second inner layer downwards. The fourth inner layer comprises a water permeable unwoven material such as cotton gauze. The third and fourth inner layers should comprise materials sufficiently translucent to permit viewing therethrough of the guide line the second inner layer.

Figure 4:
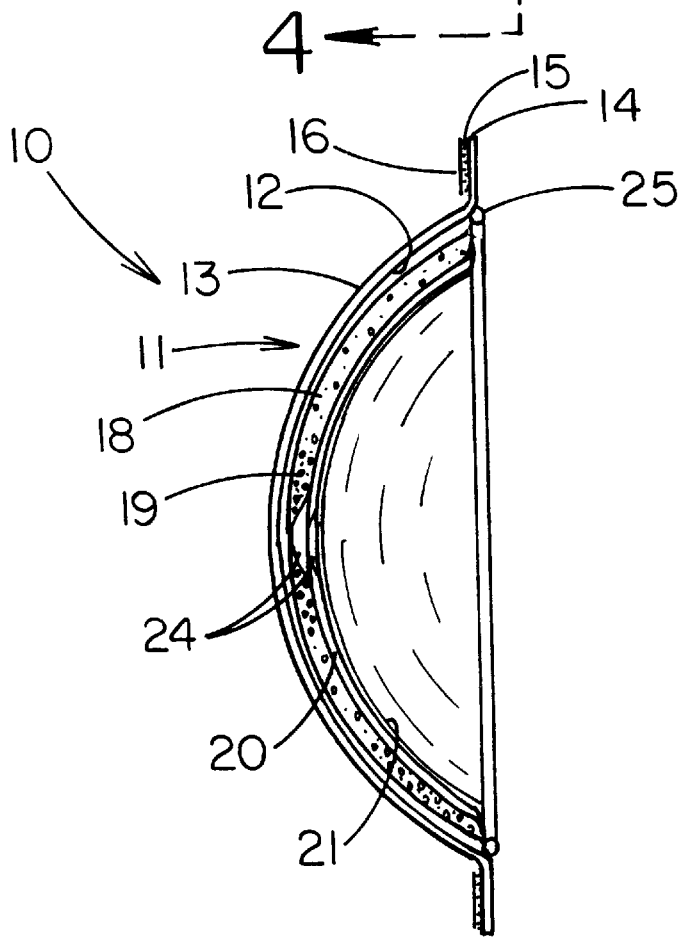
FIG. 4 is a schematic cross sectional view of the present invention taken from line 4—4 of FIG. 3.

The second, third and fourth inner layers each have a nipple receiving depression 24 located at the center of the respective inner layer. The nipple receiving depressions are coextensive with one another and extend towards the exterior layer as illustrated in FIG. 4. In use, the nipple receiving depressions define a depression in the inner space designed for receiving the nipple of the user's breast in the inner space.

An annular water impermeable seal 25 is disposed around the outer perimeters of the inner layer and is coupled to the outer perimeters of the inner layers and to an inner periphery of the outer perimeter of the exterior layer to coupled the outer perimeters of the inner layers and the exterior layer together. The seal is designed for preventing fluid absorbed by the inner layers to pass out through the outer perimeters of the inner layers or between the outer perimeters of the inner layers and the exterior layer.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A nursing pad adapted for attachment to a cup of a user's bra and interposed between the cup of the bra and the user's breast received in the cup of the bra, said nursing pad comprising:

an exterior layer having a center region, an outer perimeter, a concave inner face, and a convex outer face, said inner face of said exterior layer defining an inner space;

said exterior layer comprising a flexible water impermeable material;

a plurality of coextensive generally hemispherical inner layers being disposed in said inner space of said exterior layer;

said plurality of inner layers comprising first, second, third and fourth inner layers, said first inner layer being positioned adjacent said inner face of said exterior layer, said second and third inner layers being interposed between said first and fourth inner layers, said third inner layer being interposed between said second and fourth inner layers;

said first and third inner layer comprising a woven fabric material;

said second inner layer comprising a water absorbing material; and said fourth inner layer comprising a water permeable material.

2. The nursing pad of claim 1, wherein said exterior layer has an outwardly radiating annular outer flange around said outer perimeter of said exterior layer, and wherein said outer face of said exterior layer having an adhesive provided thereon along said outer flange of said exterior layer.

3. The nursing pad of claim 2, wherein said outer flange of said exterior layer has a plurality of apertures therethrough extending between said inner and outer faces of said exterior layer.

4. The nursing pad of claim 1, wherein said second inner layer has a lower region comprising a water absorbent material having a greater absorption capacity than a remainder region of said second inner layer.

5. The nursing pad of claim 4, wherein said second inner layer having a guide line displayed on a face of said second inner layer facing outwards away from said inner face of said exterior layer, said guide line being positioned between said lower region of said second inner layer and said center of said second inner layer.

6. The nursing pad of claim 1, wherein said second, third and fourth inner layers each have a nipple receiving depressions located at the center of the respective inner layer, said nipple receiving depressions being coextensive with one another and extending towards said exterior layer.

7. The nursing pad of claim 1, further comprising an annular water impermeable seal being disposed around said outer perimeters of said inner layer and being coupled to said outer perimeters of said inner layers and to an inner periphery of said outer perimeter of said exterior layer to coupled said outer perimeters of said inner layers and said exterior layer together.

8. A nursing pad adapted for attachment to a cup of a user's bra and interposed between the cup of the bra and the user's breast received in the cup of the bra, said nursing pad comprising:

a generally hemispherical exterior layer having a center region, a generally circular outer perimeter, a concave inner face, and a convex outer face;

said exterior layer having an outwardly radiating annular outer flange around said outer perimeter of said exterior layer;

said outer face of said exterior layer having an adhesive provided thereon along said outer flange of said exterior layer;

said adhesive of said exterior layer being adapted for adhesively coupling said outer flange to a cup of a bra of a user;

said exterior layer comprising a flexible water impermeable material;

said outer flange of said exterior layer having a plurality of apertures therethrough extending between said inner and outer faces of said exterior layer;

said concave inner face of said exterior layer defining a generally hemispherical inner space;

a plurality of coextensive generally hemispherical inner layers being disposed in said inner space of said exterior layer;

said plurality of inner layers comprising first, second, third and fourth inner layers each having centers coaxial with said center of said center of said exterior layer and each having a generally outer perimeter located inside and concentric with said outer perimeter of said exterior layer;

said first inner layer being positioned adjacent said inner face of said exterior layer, said second and third inner layers being interposed between said first and fourth inner layers, said third inner layer being interposed between said second and fourth inner layers;

said first and third inner layer comprising a woven fabric material;

said second inner layer comprising a water absorbing material, said second inner layer having a lower region comprising a water absorbent material having a greater absorption capacity than a remainder region of said second inner layer;

said second inner layer having a guide line displayed on a face of said second inner layer facing outwards away from said inner face of said exterior layer, said guide line being positioned between said lower region of said second inner layer and said center of said second inner layer;

said fourth inner layer comprising a water permeable material;

said second, third and fourth inner layers each having a nipple receiving depressions located at the center of the respective inner layer, said nipple receiving depressions being coextensive with one another and extending towards said exterior layer; and an annular water impermeable seal being disposed around said outer perimeters of said inner layer and being coupled to said outer perimeters of said inner layers and to an inner periphery of said outer perimeter of said exterior layer to coupled said outer perimeters of said inner layers and said exterior layer together.

* * * * *